(12) United States Patent
Cox

(10) Patent No.: US 6,592,592 B1
(45) Date of Patent: Jul. 15, 2003

(54) DELIVERY SYSTEM FOR BALLOON EXPANDABLE STENT

(75) Inventor: Daniel L. Cox, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/294,281

(22) Filed: Apr. 19, 1999

(51) Int. Cl.$^7$ .......................... A61F 11/00; A61M 29/00
(52) U.S. Cl. ........................................ 606/108; 606/198
(58) Field of Search ........................... 604/96.01, 103.1, 604/103.2, 194, 264, 523, 509, 104, 907, 915; 606/191–192, 194–195, 198, 108

(56) References Cited

U.S. PATENT DOCUMENTS

| | | | |
|---|---|---|---|
| 5,653,691 A | * 8/1997 | Rupp et al. | ..................... 604/96 |
| 5,759,474 A | * 6/1998 | Rupp et al. | |
| 5,968,069 A | * 10/1999 | Dusbabek et al. | .......... 606/194 |
| 6,007,543 A | * 12/1999 | Ellis et al. | |
| 6,096,056 A | * 8/2000 | Brown | ........................ 606/194 |
| 6,123,712 A | * 9/2000 | Di Caprio et al. | .......... 606/108 |
| 6,193,727 B1 | * 2/2001 | Foreman et al. | |
| 6,375,660 B1 | * 4/2002 | Fischell et al. | .............. 606/108 |

FOREIGN PATENT DOCUMENTS

WO    WO 98/07390    * 2/1998

* cited by examiner

Primary Examiner—Brian L. Casler
Assistant Examiner—Catherine Serke
(74) Attorney, Agent, or Firm—Fulwider Patton Lee & Utecht, LLP

(57) ABSTRACT

A compliant membrane is positioned between the interior of an expandable balloon and the inner member of a catheter. The membrane provides a compliant substrate onto which a stent is crimped onto the balloon over the area of the membrane. The compliant membrane effectively retains the stent on the catheter while the stent is being delivered through the vasculature. The retaining force from using a compliant membrane can be obtained by partially filling apertures as described. However, an enhanced retaining force is obtained without this effect. The membrane allows a higher normal force between the stent and balloon because of its compliance. A stent cannot be tightly crimped onto a rigid surface or tube because the elastic recoil of the stent prevents this. The compliant membrane has enough give to compensate for this small but significant elastic recoil. Essentially, the stent is squeezed onto the balloon/membrane slightly more than the final result to obtain a good gripping force. The membrane acts like a spring so that thicker membranes give higher forces because they allow the "spring" to deform more.

10 Claims, 4 Drawing Sheets

DELIVERY SYSTEM FOR BALLOON EXPANDABLE STENT

BACKGROUND OF THE INVENTION

The invention relates generally to stent delivery systems including catheters similar to the kind used, for example, in percutaneous transluminal coronary angioplasty ("PTCA") procedures. More particularly, the invention pertains to the use of a compliant membrane for retaining the stent on the catheter during delivery through the patient's vascular system.

In typical PTCA procedures, a guiding catheter is percutaneously introduced into the cardiovascular system of a patient through the brachial or femoral arteries and advanced therethrough until the distal end thereof is in the ostium of the desired coronary artery. A guide wire and a dilatation catheter having a balloon on the distal end thereof are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the lesion. Once in position across the lesion, the flexible, expandable, preformed balloon is inflated to a predetermined size with radiopaque liquid at relatively high pressures (e.g., greater than about 4 atmospheres) to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery.

In angioplasty procedures of the kind referenced above, there may be restenosis of the artery, which either necessitates another angioplasty procedure, a surgical bypass operation, or some method of repairing or strengthening the area. To reduce the likelihood of the development of restenosis and strengthen the area, a physician can implant an intravascular prosthesis for maintaining vascular patency, called a stent, inside the artery at the lesion. The stent is expanded to a larger diameter, often by the balloon portion of the catheter. Stents delivered to a restricted coronary artery, expanded to a larger diameter by a balloon catheter, and left in place in the artery at the site of a dilated lesion are well known in the art as are various delivery systems used to deliver and implant a stent. Typical stent delivery systems can be found in U.S. Pat. No. 5,514,154 (Lau et al.).

A shortcoming of previously known stent delivery systems is the possibility of the stent shifting off the balloon while being maneuvered through a patient's vasculature. Contact with plaque or other obstructions encountered within the vasculature pose a risk of impeding the progress of the stent while the underlying balloon and catheter continue to be advanced. Stent shifting on the balloon or stent loss also exists when trying to retract the stent into the guiding catheter in the event the stent could not be delivered.

In one prior art device stent shifting or stent loss has been addressed with the use of an elastomeric protective membrane that is disposed about the balloon and attached to the catheter. In addition to controlling the shape of the balloon, protecting the balloon and containing any debris should the balloon rupture, the membrane provides a pliable surface into which the unexpanded stent can be crimped. This results in an enhanced grip that more effectively prevents the stent from being prematurely dislodged from about the balloon prior to inflation.

Disadvantages associated with such approach include the potential for the membrane to interfere with the performance of the balloon. Because the membrane is located between the balloon and stent, the stent conceivably may become so imbedded in the membrane during inflation of the balloon by virtue of the substantial pressure exerted by the balloon against the stent such that stent fails to completely detach from the membrane upon deflation of the balloon. This may prevent the retraction of the delivery system after the stent has been irreversibly expanded against the vessel walls. Additionally, the surface texture of the compliant membrane may also generate undesirable friction between the membrane and the stent as the delivery system is being withdrawn and between the membrane and the vessel walls as it is withdrawn therethrough.

Other prior art catheter systems have shoulders or rings on the balloon at either end of the stent to help hold the stent in place, but such devices have a high profile. A protective retractable sheath over the balloon and stent is also known in the art but such systems have a high profile and are much less flexible and therefore are more difficult to deliver in the patient's vasculature.

An improved stent delivery system is needed that takes full advantage of the balloon's low friction surface, allows a stent to firmly grip the delivery balloon catheter, positively ensures stent release after deployment and deflation of the balloon, provides a low profile, and ensures flexibility of distal portion of the stent delivery catheter.

SUMMARY OF THE INVENTION

The present invention is directed to the use of an elastic or pliable membrane that provides a compressible mass into which a stent can be crimped to ensure its retention about a delivery catheter and balloon. The membrane is positioned within the expandable balloon in the form of a tubular sheath affixed about the underlying catheter.

The compliant membrane into which the struts of the stent are crimped provide substantially more friction to retain the stent than is achieved by the extremely thin and virtually frictionless surface of the balloon. Additionally, because the membrane is positioned within the balloon, it does not in any way participate in nor can it interfere with the deployment of the stent. In fact, during inflation of the balloon, the balloon serves to effectively separate the stent from the membrane. This ensures that the delivery system can easily be withdrawn from the vasculature. Moreover, the slippery nature of the outer surface of the balloon can be taken full advantage of when withdrawing the catheter delivery system after deployment of the stent.

In one preferred embodiment, a delivery catheter has an expandable balloon adjacent its distal end. The catheter preferably has an inner member and an outer member at least in the region of the distal portion of the catheter, the inner and outer members having a coaxial relationship. An elastic membrane positioned on the inner member in the area of the balloon so that the stent, which is mounted and crimped on the balloon, is positioned over the elastic membrane. Preferably, the membrane is thin, highly elastic, and has a diameter smaller than the inner member so that it tightly grips the inner member and will not shift. While it is preferred that the membrane has a uniform thickness, the ends of the membrane that extend beyond the stent can be thicker thereby forming a ridge on either end of the stent to protect the ends and prevent stent shifting or stent loss. As the stent is crimped tightly onto the balloon, the elastic membrane tries to fill the spaces between the stent struts, thereby providing a gripping action on the stent.

A number of different membrane configurations may be employed to practice the present invention including embodiments wherein the membrane is shorter, longer, or of the same length as the stent. Each such embodiment provides certain advantages relating to the amount of gripping force afforded thereby and to the smoothness of the profile of the resulting assembly. Further, the membrane may have proximal, distal and center sections that align with the stent to provide the required gripping force. The membrane may have a radiopaque material impregnated in or coated on it to more easily identify the position of the stent in the vasculature.

DETAILED DESCRIPTION OF THE PREFERRED EMBODIMENTS

As shown in FIGS. 1–8, the stent delivery system of the present invention facilitates retaining the stent on a balloon while maneuvering the stent into position within a patient's vasculature, and it subsequently serves to expand the stent by inflation of the underlying balloon and finally provides for its unencumbered removal from the vasculature to leave the expanded stent in place. Each embodiment of the invention is shown both in its expanded state in order to provide a clear view of its structure and in its collapsed state in order to illustrate the interaction between the stent and the delivery system.

Figure 1:
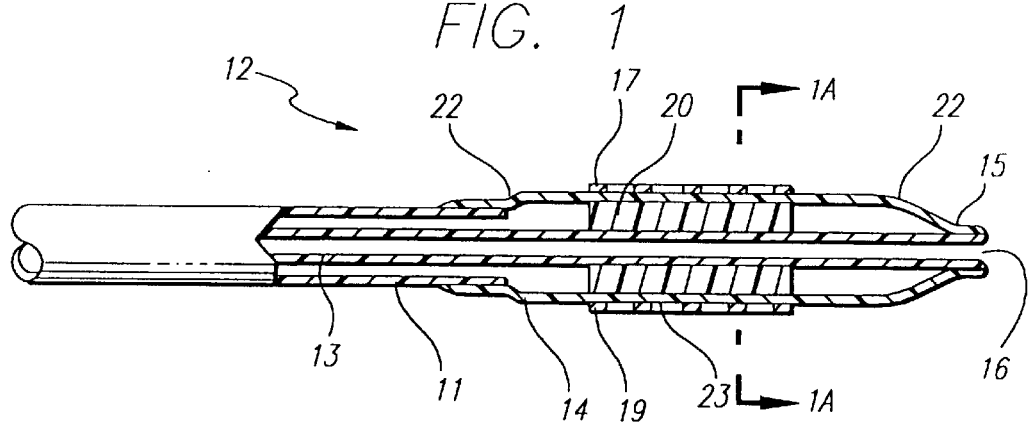
FIG. 1 is a partial cross-sectional view of one embodiment of the resent invention depicting the stent tightly crimped onto the balloon wherein the membrane is substantially the same length as the stent.
Figure 1A:
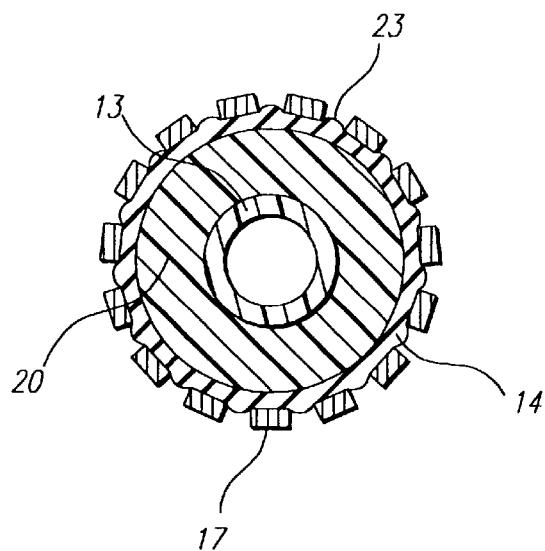
FIG. 1A is a cross-sectional view taken along lines 1A—1A depicting the membrane providing a gripping force on the stent.
Figure 2:
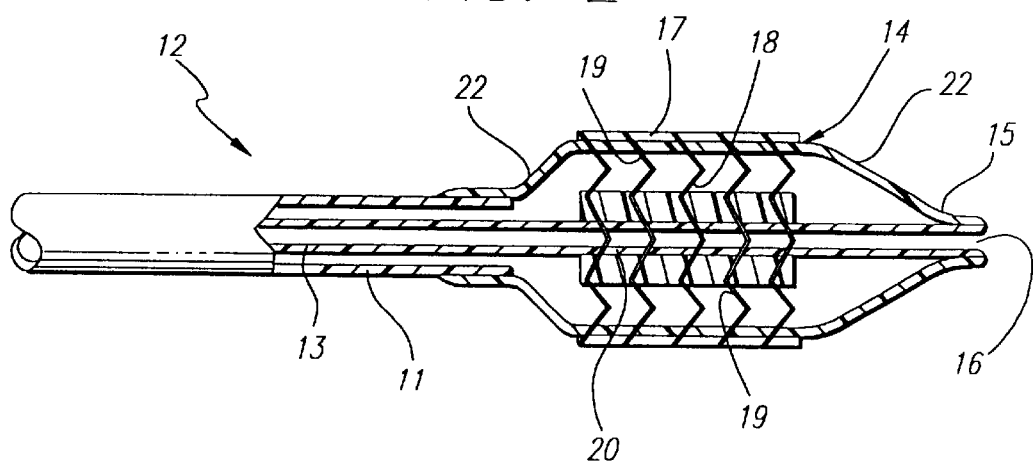
FIG. 2 is a partial cross-sectional view showing the embodiment of FIG. 1 after inflation of the balloon.

FIGS. 1 and 2 illustrate one preferred embodiment of the present invention in which catheter 12, having an inflation balloon 14 positioned near its distal end 16, has stent 17 disposed thereabout. Within the balloon and about the catheter is disposed an elastomeric membrane 20. Preferably, catheter 12 includes outer member 11 and inner member 13 arranged in a co-axial configuration at least in distal portion 15 of the catheter. In this embodiment, the length of the membrane substantially corresponds to that of the stent and membrane 20 is tightly affixed to inner member 13. As shown in FIGS. 1 and 1A, this enables the crimped stent to engage the underlying structure along its entire length and thereby maximize its grip on the delivery system.

Both the balloon 14 and balloon taper 22 are initially collapsed against inner member 13 of the catheter. The elastomeric membrane has a high degree of resiliency and provides a cushion as the stent is tightly crimped onto the balloon and over the membrane. Stent 17 preferably has an open lattice configuration having stent struts 18 forming apertures 19, so that as the stent is crimped onto the balloon, the membrane at least partially fills apertures 19 in the stent. Thus, even though the stent mounted on the balloon is not directly in contact with the membrane, it is nonetheless firmly held on the balloon since the membrane, because of its resiliency, has a tendency to at least partially fill some of the stent apertures, forming bulges 23 into the apertures as shown in FIG. 1A. Each of the compliant membrane embodiments discussed herein provide similar retaining force as shown in FIG. 1A.

Figure 3:
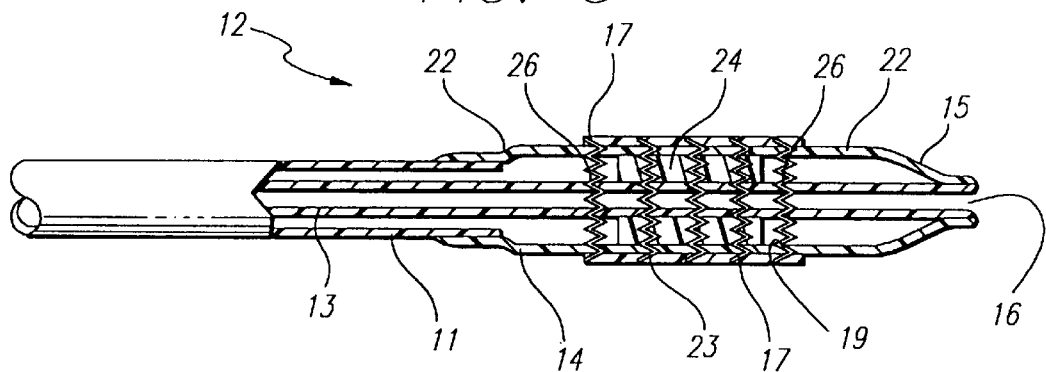
FIG. 3 is a partial cross-sectional view of another embodiment of the present invention depicting the stent tightly crimped onto the balloon wherein the membrane is shorter than the stent.
Figure 4:
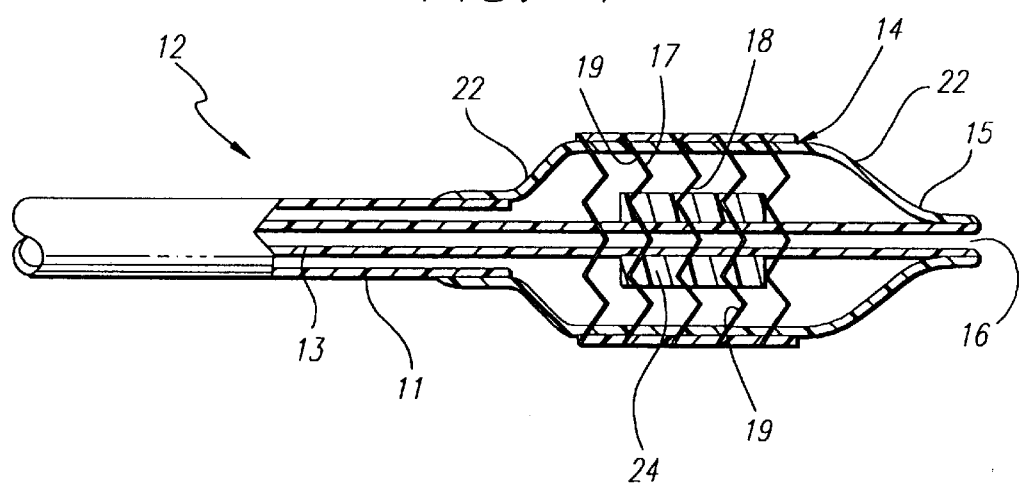
FIG. 4 is a partial cross-sectional view showing the embodiment of FIG. 3 after inflation of the balloon.

FIGS. 3 and 4 illustrate another embodiment wherein the length of elastomeric membrane 24 is selected to be shorter than the length of stent 17. The advantages of such configuration are apparent in FIG. 3. The absence of membrane near stent ends 26 allows the stent ends to be crimped to a smaller diameter than the center section of the stent. The resulting stent profile reduces the risk that the stent ends will snag on any obstructions that may be encountered while the stent is being delivered through the vasculature.

Figure 5:
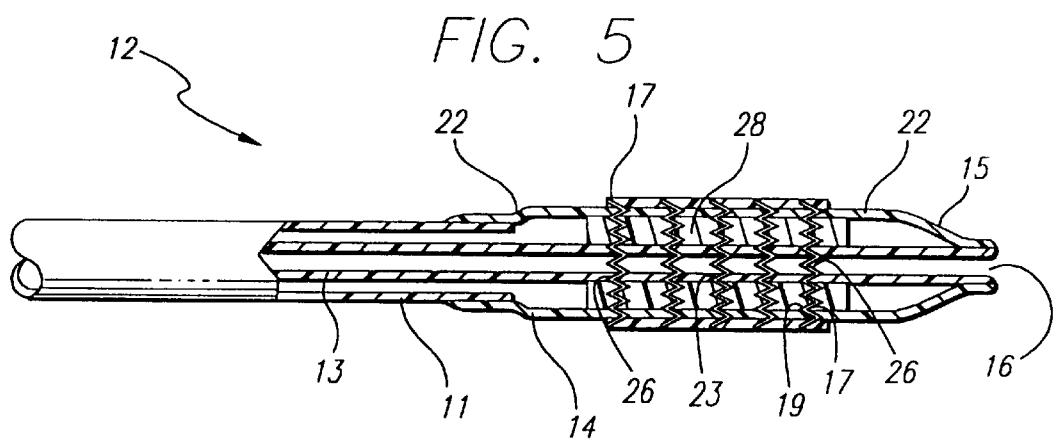
FIG. 5 is a partial cross-sectional view of one embodiment of the present invention depicting the stent tightly crimped onto the balloon wherein the membrane is longer than the stent.
Figure 6:
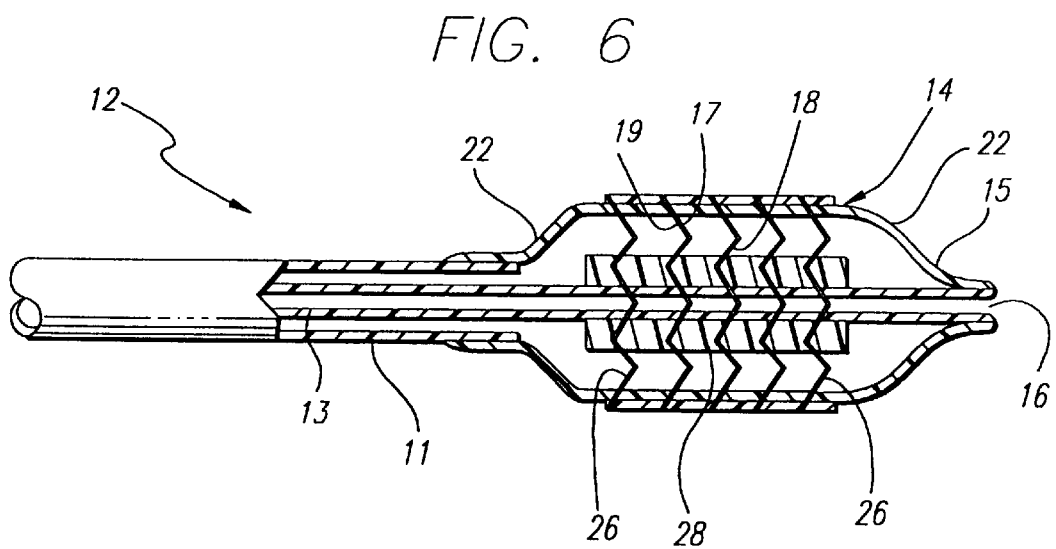
FIG. 6 is a partial cross-sectional view showing the embodiment of FIG. 5 after inflation of the balloon.

FIGS. 5 and 6 illustrate a further embodiment wherein elastomeric membrane 28 is attached to inner member 13 and is longer than stent 17. The presence of the membrane beyond stent ends 26 provides a balloon profile that is slightly larger distal and proximal to the stent. Thus, in this embodiment, the tightly crimped stent squeezes the membrane so that the membrane bulges out 27 slightly past the stent ends resulting in an overall substantially uniform profile along the stent and balloon, with the stent ends being protected by the bulges in the membrane.

Figure 7:
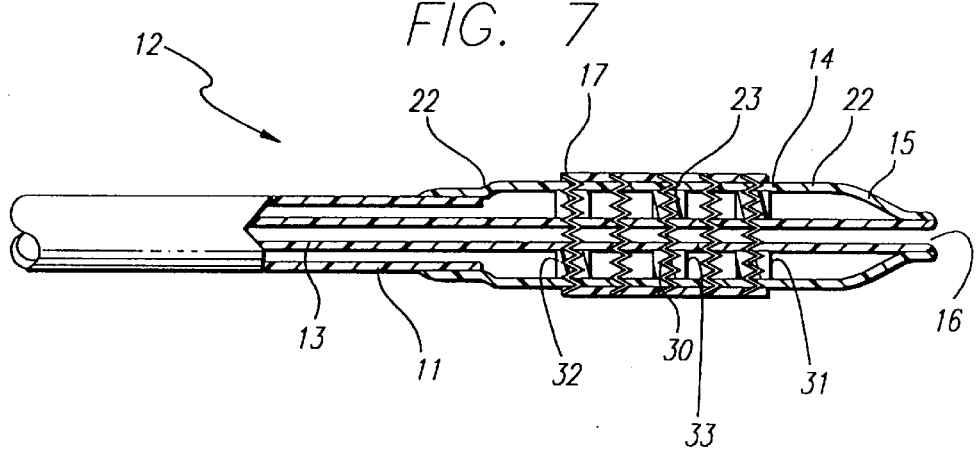
FIG. 7 is a partial cross-sectional view of one embodiment of the present invention depicting the tightly crimped stent onto the balloon wherein the membrane has proximal, distal and center sections aligned with the stent.
Figure 8:
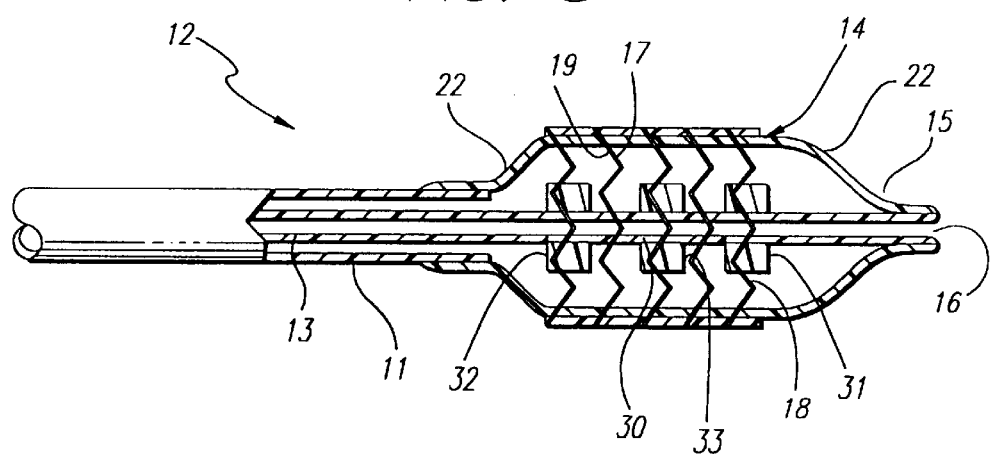
FIG. 8 is a partial cross-sectional view showing the embodiment of FIG. 7 after inflation of the balloon.

In another embodiment of the invention, as shown in FIGS. 7 and 8, elastomeric membrane 30 has multiple sections including distal section 31, proximal section 32, and center section 33. The various sections are attached to inner member 13, preferably so that the center section aligns with the center of the stent and the proximal and distal sections align with the stent ends 26. Alternatively, the distal and proximal sections can extend beyond the stent ends to protect the stent ends from the vasculature as stent 17 is delivered.

The diameter and thickness of the elastomeric membrane in each embodiment must be selected in view of the particular application in which it is to be utilized. The inner diameter of the membrane should be smaller than the outer diameter of the inner member of the catheter to ensure a tight fit thereabout. On the other hand, the selected wall thickness is a trade-off between the desired grip strength, wherein a thicker membrane provides more grip by filling the stent apertures, and the overall diameter of stent while crimped about the catheter. The retaining force from using a compliant membrane can be obtained by partially filling apertures as described. However, an enhanced retaining force is obtained without this effect. The membrane allows a higher normal force between the stent and balloon because of its compliance. A stent cannot be tightly crimped onto a rigid surface or tube because the elastic recoil of the stent prevents this. The compliant membrane has enough give to compensate for this small but significant elastic recoil. Essentially, the stent is squeezed onto the balloon/membrane slightly more than the final result to obtain a good gripping force. The membrane acts like a spring so that thicker membranes give higher forces because they allow the "spring" to deform more.

The balloon material also influences the selection of such membrane parameters as an extremely slippery balloon material or balloon coating requires enhanced compliance of the membrane in order to achieve a desired level of grip. Selection of the durometer of the membrane also has an effect on the amount of grip that can be realized, wherein more resilient material allows the stent to be crimped deeper into the membrane substrate.

The elastomeric membrane preferably is one that has a high degree of linearity (non-plasticity) for a wide range of stress and strain values. In the preferred embodiment, however, any elastic material may be used. Commercially available tubing such as "C-Flex" tubing may be used. "C-Flex" tubing may be obtained from Concept Polymer Technologies of Largo, Fla. Other suitable materials include silicones, latexes, urethanes, polysiloxane modified styrene-ethylene/butylene-styrene block copolymers (SEBS) and their associated families.

The material forming the membrane may also be impregnated with a radiopaque marker material, or made from a radiopaque material. Suitable radiopaque materials include iodine based materials and barium salts, including materials containing iodipamid (sold commercially under the trade name Cholografin), iopanoic acid (sold under the trade name Telepaque), barium sulfate, bismuth trioxide, bismuth oxychloride, or powdered metals, such as tantalum. By making the membrane radiopaque the location of the stent in the vasculature is more easily determined.

The membrane may be attached to the catheter by adhesive. Alternatively, the membrane may be affixed to the catheter without the use of adhesives by for example, shrink fitting. As an example of a method of shrink fitting the elastic membrane onto a PTCA catheter, a silicon tube with an inner diameter slightly smaller than the diameter of the catheter inner diameter is attached to the inner member by first immersing the silicone tubing into an alcohol or Freon™ bath. The silicon absorbs the Freon™ readily and swells in addition to softening. Because of the swelling, the inner diameter of the silicone tubing increases, allowing the tubing to slide over the inner member. As the Freon™ evaporates from the silicone, the tubing shrinks to its original dimensions, thus, a shrink fit is created between the silicone tubing membrane and the inner member. As compared to an alcohol bath, Freon™ expands silicone more than alcohol and it also dissolves Microglide™ better than alcohol (Microglide™ is a coating to reduce friction).

In addition, it is possible to slide the tubing over the catheter inner member after immersing the tubing in alcohol. It is possible that the alcohol may dissolve some of the lubricating coating often found on a dilatation catheter shaft, such as a Microglide™ Coating, manufactured by Advanced Cardiovascular Systems, Inc. (ACS) of Santa Clara, Calif. The alcohol lubricates the sheath during the assembly process then evaporates readily.

Though in the preferred embodiments the elastic material is shown in a tubular shape, the elastic material may also be applied in a band or strip form, to surround the catheter inner member as a winding. Alternatively, the elastic material may be deposited or coated chemically onto the catheter.

The catheter 12 as described herein can have an over-the-wire ("OTW") or rapid exchange (Rx) configuration as more fully disclosed in U.S. Pat. No. 4,323,071 (Simpson et al.) (OTW); U.S. Pat. No. 4,573,470 (Samson et al.) (OTW); U.S. Pat. No. 5,501,227 (Yock) (Rx); U.S. Pat. No. 5,061, 273 (Yock) (Rx); and U.S. Pat. No. 5,496,346 (Horzewski et al.) (Rx), which are incorporated herein in their entirety by reference thereto.

The stent 17 as described herein can have various configurations and suitable stents include the ACS Multi-Link Stent sold by Advanced Cardiovascular Systems, Inc., Santa Clara, Calif.; the NIR Stent sold by Boston Scientific, Natick, Mass.; and the Micro Stent II and GFX sold by Arterial Vascular Engineering, Santa Rosa, Calif. The ACS Multi-Link Stent mounted on a rapid exchange delivery catheter is disclosed in U.S. Pat. No. 5,514,154 (Lau et al.), which is incorporated herein by reference.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. A delivery system for a balloon expandable stent, comprising:
    a catheter;
    at least two separate membranes disposed about said catheter wherein such membranes are selected to have a sufficient amount of compliance such that a stent, constructed of struts that define spaces there between, that is crimped thereabout is capable of maintaining said membranes in a deformed state wherein said membranes extend into said spaces to mechanically interlock said stent to said membranes; and
    an inflatable balloon disposed about said membranes, whereby a stent, positioned about said balloon can be crimped to a diameter that compresses said membranes to provide enhanced grip between the balloon and the stent.

2. The delivery system of claim 1, wherein said catheter has an outer member and an inner member arranged in a coaxial configuration in at least a distal section of said catheter.

3. The delivery system of claim 2, wherein said at least two separate membranes are attached to said inner member.

4. The delivery system of claim 1, wherein said at least two separate membranes include a distal membrane section, a proximal membrane section and a center membrane section.

5. The delivery system of claim 1, wherein said stent has a plurality of apertures, said stent being tightly crimped onto said balloon so that said at least two separate membranes form bulges into said apertures thereby providing a gripping force on said stent.

6. An endovascular device, comprising:
    a catheter assembly;
    a membrane concentrically fitted about said catheter wherein such membrane is selected to have a sufficient amount of compliance such that a stent having a tubular structure with a first end and a second end, constructed of struts that define spaces there between, that is crimped thereabout is capable of maintaining said membrane in a deformed state and of causing said membrane to extend into said spaces to mechanically lock said stent to said membrane, the membrane being shorter in length than said stent thereby allowing said ends of said stent to be crimped to a diameter smaller than the rest of said stent;
    an inflatable balloon concentrically fitted about said membrane; and
    an expandable stent concentrically fitted about said balloon wherein said stent is initially reduced in diameter by crimping so as to tightly confine the balloon, membrane and stent thereby enabling said catheter assembly to be maneuvered through vasculature and wherein inflation of said balloon expands said stent away from said membrane.

7. The device of claim 6, wherein said catheter assembly has an outer member and an inner member which are co-axially aligned at least in a distal section of said catheter assembly, the membrane being attached to said inner member.

8. A delivery system for a balloon expandable stent of preselected length, wherein such stent is constructed of struts that define spaces there between, comprising:

a catheter;

a compliant membrane, disposed about said catheter and sufficiently compliant so as to extend into said spaces when said stent is crimped there about to mechanically lock said stent to said membrane, said compliant membrane comprises radiopaque material; and an inflatable balloon disposed about said membrane, whereby said stent, positioned about said balloon can be crimped to a diameter that compresses said membrane to provide an enhanced grip between the balloon and the stent.

9. The delivery system of claim 8, wherein said membrane and said stent are of equal length.

10. The delivery system of claim 8, wherein said membrane is longer than said stent.

* * * * *

UNITED STATES PATENT AND TRADEMARK OFFICE
CERTIFICATE OF CORRECTION

PATENT NO.    : 6,592,592 B1
DATED         : July 15, 2003
INVENTOR(S)   : Daniel L. Cox It is certified that error appears in the above-identified patent and that said Letters Patent is hereby corrected as shown below:

<u>Title page,</u>
Item [56], References Cited, U.S. PATENT DOCUMENTS, add the U.S. Patents listed below:

| Patent No. | Date | Inventor |
|---|---|---|
| 2,701,559 | 02/08/55 | Cooper |
| 3,045,677 | 07/24/62 | Wallace |
| 4,199,646 | 04/22/80 | Hori et al. |
| 4,338,942 | 07/13/82 | Fogarty |
| 4,553,545 | 11/19/85 | Maass et al. |
| 4,702,252 | 10/27/87 | Brooks et al. |
| 4,710,181 | 12/01/87 | Fuqua |
| 4,732,152 | 03/22/88 | Wallsten et al. |
| 4,733,665 | 03/29/88 | Palmaz |
| 4,800,882 | 01/31/89 | Gianturco |
| 4,880,683 | 11/14/89 | Stow |
| 4,950,227 | 08/21/90 | Savin et al. |
| 4,976,720 | 12/11/90 | Machold et al. |
| 5,015,231 | 05/14/91 | Keith et al. |
| 5,049,132 | 09/17/91 | Shaffer et al. |
| 5,078,720 | 01/07/92 | Burton et al. |
| 5,100,386 | 03/31/92 | Inoue |
| 5,100,429 | 03/31/92 | Sinofsky et al. |
| 5,102,402 | 04/07/92 | Dror et al. |
| 5,108,416 | 04/28/92 | Ryan et al. |
| 5,116,318 | 05/26/92 | Hillstead |
| 5,135,536 | 08/04/92 | Hillstead |
| 5,156,911 | 10/20/92 | Stewart |
| 5,158,548 | 10/27/92 | Lau et al. |
| 5,195,969 | 03/23/93 | Wang et al. |
| 5,242,394 | 09/07/93 | Tremulis |
| 5,242,399 | 09/07/93 | Lau et al. |
| 5,270,086 | 12/14/93 | Hamlin |
| 5,344,426 | 09/06/94 | Lau et al. |

UNITED STATES PATENT AND TRADEMARK OFFICE
CERTIFICATE OF CORRECTION

PATENT NO. : 6,592,592 B1
DATED : July 15, 2003
INVENTOR(S) : Daniel L. Cox

It is certified that error appears in the above-identified patent and that said Letters Patent is hereby corrected as shown below:

<u>Title page (cont'd),</u>
Item [56], References Cited, U.S. PATENT DOCUMENTS, add the U.S. Patents listed below:

| Patent No. | Date | Inventor |
|---|---|---|
| 5,360,401 | 11/01/94 | Turnland |
| 5,372,600 | 12/13/94 | Beyar et al. |
| 5,387,450 | 02/07/95 | Stewart |
| 5,412,035 | 05/02/95 | Schmitt |
| 5,423,745 | 06/13/95 | Todd et al. |
| 5,445,646 | 08/29/95 | Euteneuer et al. |
| 5,458,615 | 10/17/95 | Klemm et al. |
| 5,507,768 | 04/16/96 | Lau et al. |
| 5,514,154 | 05/07/96 | Lau et al. |
| 5,545,132 | 08/13/96 | Fagan et al. |
| 5,571,135 | 11/05/96 | Fraser et al. |
| 5,626,604 | 05/06/97 | Cotton, Jr. |
| 5,653,690 | 08/05/97 | Booth et al. |
| 5,720,726 | 02/24/98 | Marcadis et al. |
| 5,801,871 | 09/22/98 | Tuckey et al. |
| 5,830,217 | 11/03/98 | Ryan |
| 5,836,965 | 11/17/98 | Jendersee et al. |
| 5,893,852 | 04/13/99 | Morales |

UNITED STATES PATENT AND TRADEMARK OFFICE
CERTIFICATE OF CORRECTION

PATENT NO. : 6,592,592 B1
DATED : July 15, 2003
INVENTOR(S) : Daniel L. Cox

It is certified that error appears in the above-identified patent and that said Letters Patent is hereby corrected as shown below:

Title page (cont'd),
FOREIGN PATENT DOCUMENTS, add:
-- EP  0 897 730   2/1999
   EP  0 901 776   3/1999
   EP  0 974 315   1/2000

693,224         06/24/53       Great Britain 0 292 587       11/30/88       European Patent Office 0 428 479 A1    05/22/91       European Patent Office 0 461 474 B1    12/18/91       European Patent Office
                                                        --.

OTHER PUBLICATIONS,
-- Application for U.S. Letters Patent Serial No. 09/245,4499 filed February 5, 1999 --.

Signed and Sealed this

Twenty-third Day of December, 2003

JAMES E. ROGAN
*Director of the United States Patent and Trademark Office*